(12) United States Patent
Ajioka et al.

(10) Patent No.: US 8,436,025 B2
(45) Date of Patent: May 7, 2013

(54) COMPOUNDS AND METHODS FOR PKC THETA INHIBITION

(75) Inventors: Janet Ajioka, Seattle, WA (US); Heidi S. Hummel, Seattle, WA (US); Rich B. Meyer, San Mateo, CA (US); John Swindle, Seattle, WA (US)

(73) Assignee: CompleGen Partners, Inc., Seattle, WA (US)

( * ) Notice: Subject to any disclaimer, the term of this patent is extended or adjusted under 35 U.S.C. 154(b) by 285 days.

(21) Appl. No.: 12/561,750

(22) Filed: Sep. 17, 2009

(65) Prior Publication Data

US 2010/0120869 A1 May 13, 2010

Related U.S. Application Data

(60) Provisional application No. 61/098,640, filed on Sep. 19, 2008.

(51) Int. Cl.
*A61K 31/136* (2006.01)
*A61K 31/4412* (2006.01)
*A61P 29/00* (2006.01)
*A61P 37/06* (2006.01)
*A61P 3/10* (2006.01)

(52) U.S. Cl.
USPC .................................. 514/349; 514/646

(58) Field of Classification Search .......... None
See application file for complete search history.

(56) References Cited

U.S. PATENT DOCUMENTS

| 2004/0192743 A1* | 9/2004 | Mjalli et al. ............... 514/365 |
| 2006/0009453 A1 | 1/2006 | Geuns-Meyer et al. |
| 2006/0025433 A1 | 2/2006 | Barbosa et al. |
| 2007/0287738 A1 | 12/2007 | Cole et al. |
| 2008/0027061 A1 | 1/2008 | Riedl et al. |

FOREIGN PATENT DOCUMENTS

| WO | WO00/59878 | * 10/2000 |
| WO | WO03/075921 | * 9/2003 |

OTHER PUBLICATIONS

Kumar et al. In Leprosy in India (1983) Jul:55(3):465-471.*
Dapsone Structure' in www.chemsynthesis.com/base/chemical-structure-14034.html.*
Seydel et al. In Quantitative Structure-Activity and Structure-Toxicity Relationships 18(1), 43-51 (1999).*
International Search Report dated Nov. 2, 2009 issued in related International Patent Application No. PCT/US2009/057240, filed Sep. 17, 2009.

* cited by examiner

*Primary Examiner* — Dennis Heyer
(74) *Attorney, Agent, or Firm* — Kilpatrick Townsend & Stockton LLP.

(57) ABSTRACT

The present invention provides a method of selectively inhibiting PKCθ in the presence of PKCδ, by administering to a subject in need thereof, a therapeutically effective amount of a compound of Formula I. The present invention also provides a method of inhibiting cytokine synthesis in a T cell, a method of inhibiting T cell proliferation, and a method of inhibiting the replication of and cytokine production by T lymphocytes, while not stimulating or inhibiting the replication of B lymphocytes.

4 Claims, 11 Drawing Sheets

Scheme 1. Synthesis of -4-(substituted phenoxy)-anilines (4)

Scheme 2. Synthesis of 4-(halogenated phenoxy)-anilines (8)

Scheme 3. Synthesis of 4-(substituted phenylthio)-anilines (12)

Scheme 4. Synthesis of 4-[substituted (phenylsulfinyl and phenylsulfonyl)]-anilines (13 and 14, respectively)

Scheme 5. Synthesis of N-acylated aniline-2, 5-dichlorophenyl ether

Scheme 6. Synthesis of N-(2, 4-dichlorophenoxyphenyl)urea

Scheme 7. Synthesis of N-acylated 4-(substituted phenylthio)anilines ether. 4-(tert-butylphenylthio)acetanilide (26)

Scheme 8. Synthesis of N-acylated 4-[substituted (phenylsulfinyl and phenylsulfonyl)]-anilines Scheme 9. Synthesis of 4'-(tert-butylphenoxy)-2-dimethylaminoacetanilide

COMPOUNDS AND METHODS FOR PKC THETA INHIBITION

CROSS-REFERENCES TO RELATED APPLICATIONS

This application claims priority to U.S. Provisional Application No. 61/098,640, filed Sep. 19, 2008, which is incorporated in its entirety herein for all purposes.

BACKGROUND OF THE INVENTION

T lymphocytes are an essential part of the immune response as they are necessary for initiating the cellular response to pathogenic organisms, host cells that have become oncogenic and damaged tissue (see Fundamental Immunology, 6$^{th}$ Edition, 2003, ed. Paul, Wm. Lippencott Williams & Wilkins). Functionally, T cells have been subdivided into two classes with distinct surface antigens, CD4 and CD8 and this differentiation occurs in the Thymus. CD4+ cells are helper T cells and are further divided into Th1, Th2 and Th17 (see Tesmer, L. A., et al. (2008) Immunological Reviews, 228,87-113, Harington, L. et al. (2005) Nat. Immunol. 6,1123) which produce distinct levels of different cytokines (see below). CD8+ cells are cytolytic cells and are involved in lysis of tumors or viral infected cells. These responses are usually initiated by the interaction of a specific surface protein of the T cell, the T cell Receptor, TCR, (Davis, M. and Bjorkman, P. (1988) Nature 334, 395) with a "foreign" antigen on a defective host cell or on an Antigen Presenting Cell, APC, in the context of surface proteins of the Major Histocompatablilty Complex I or II (MHC I or II) and other proteins in a complex structure, the Immune Synapse (Grakoui, A, et al., (1999) Science 285,221). When the TCR interacts with a cognate antigen, it triggers a series of responses leading to activation of the T cell (Weiss, A. et al. (1991) Semin. Immulol. 3, 313, Weiss, A, (2003) Ann. Rev. Immunology). Activated T cells are induced to replicate more rapidly and, especially in the case of CD4+ cells, produce signaling proteins that are stimulatory (cytokines) or chemoattractive (chemokines) to inflammatory cells (i.e. lymphocytes, PMNLs, macrophage and monocytes) (Cook, D. N. (1996) J. Leukocyte Biol. 59,61, Friedman, et al. (2006) Nat. Immunol. 7, 1101).

T cell activation can result in a disease process. In animal models T cell responses described above have been shown to result in the inflammation of various tissues leading to experimental diseases resembling, among others, asthma and COPD, rheumatoid arthritis, psoriasis, atopic dermatitis, uveitis, and multiple sclerosis. (Barnes, P. (2008) Nat. Rev. Immunol. 8,183; Martin (2003) Paediatric Respiratory Reviews, 5;S47). Furthermore, activated T cells and the relevant cytokines have been identified in the corresponding human diseases (Barnes, P (2008) Nat. Rev. Immunol. 8;183; Krueger, J G and Bowcock (2005) Ann. Rev. Rheum. Dis. 64;30,13,14). T cells are directly activated by foreign MHC I and II as well as other antigens on transplanted tissues (liver, kidney, heart, etc.) resulting in graft rejection response which can be blocked by T cell specific antibodies and/or by drugs known to block T cell activation (Odum, J. et al. (1993) Clin Nephrol. 39:230; Passerini, P. and Ponticelli, C. (2001) Curr Opin Nephrol Hypertens.10(2):189-93). T cell recruitment of macrophages is involved in pancreatic lesions leading to loss of β-cells and Type 1 diabetes (Cantor, J. and Haskins, K. (2006) Drug Discovery Today: Disease Mechanisms 3;381). In addition, T cells can become oncogenic, resulting in T cell Lymphomas and Leukemias which in many instances are fatal (see Cheson, B. (2007) Sem. In Oncol. 34sup5; S3-S7).

Following the interaction of the T cell receptor, a series of kinases and other enzymes is activated resulting in the transport to the nucleus and/or activation of the transcription factors NFkappaB, NFAT and AP1 which causes transcription of cytokine and chemokine genes, as well as genes involved in T cell replication, motility and survival (Cordronniere, N. et al. (2000) Proc. Nat. Acad. Sci. 97;3394, Wulfing, C. and Davis, M. M. (1998) Science 282;2266). The serine/threonine kinase PKC theta, is an essential step in this pathway (Sun et al. (2000) Nature 404:402-7,19) and PKC theta deficient mice do not mount a T cell-driven inflammatory response (Healy, A. M. et al. (2006) J. Immunol. 177;1886, Anderson, K. et al. (2006) Autoimmunity 39;429). Human T cell lymphomas appear to have an upregulated PKCθ pathway (Vacca, A., et al. (2006) The EMBO Jour. 25, 1000) and mice deleted for PKCθ have reduced incidence of T cell lymphoma (Felli, P. M., et al. (2005) Oncogene 24;992). Blocking the function of PKCθ may be a therapy for several diseases in which T cells are involved.

It has also been shown that PKCθ activation in skeletal muscle may be involved in Type II diabetes (Li Y., et al. (2004) J. Biol. Chem. 279;45304), hence other diseases might be ameliorated by a inhibiting PKCθ.

The PKC family of serine/threonine kinases is comprised of at least 11 members grouped into three subfamilies based on their cofactor requirements: Conventional (alpha, beta1 and 2, gamma), novel (delta, epsilon, eta, theta) and atypical (xi, iota and zeta) (Newton, A. (2003) Biochem. J. 370;361.), which are structurally similar, but are necessary for many distinct cellular processes that are essential for cellular differentiation, survival and other specific cellular functions. For example, the novel PKC delta whose structure is most similar to PKC theta, appears to be essential for regulating replication of B lymphocytes (B cells) and reduced PKC delta causes uncontrolled expansion of B cells leading to B cell invasion of tissues similar to Systemic Lupus Erythematosis (Mecklenbräuker, I. et al. (2002) Nature 416;860; Miyamoto, A., et al., (2002) Nature 416;859). Conversely, the conventional PKC beta is necessary for B cell replication and survival (Saijo, vK., et al. (2003) Ann. N.Y. Acad. Sci. 987;125). Hence, although it is apparent that blocking of PKC theta may be therapeutic for diseases involving T cell activation, there is a need for isozyme-specific PKC theta inhibitors, in particular inhibitors of PKC-theta that have minimal activity on PKC-delta and beta. Surprisingly, the present invention meets this, and other, needs.

BRIEF SUMMARY OF THE INVENTION

In one embodiment, the present invention provides a method of selectively inhibiting PKCθ in the presence of PKCδ, by administering to a subject in need thereof, a therapeutically effective amount of a compound of Formula I:

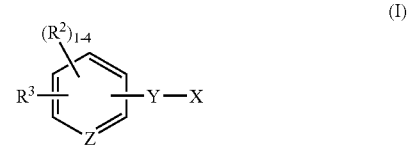

wherein X of Formula I is aryl or heteroaryl, each substituted with 1-5 R$^1$ groups. Y of Formula I is —O—, —S(O)$_n$—, —N(R$^4$)— and —C(R$^4$)$_2$—, wherein subscript n is 0-2. Z of Formula I is —N= or —CH=. Each $R^1$ of Formula I is independently from the group consisting of H, halogen, $C_{1-8}$ alkyl, $C_{1-6}$ heteroalkyl, $C_{1-6}$ haloalkyl, $C_{2-6}$ alkenyl, $C_{2-6}$ alkynyl, $C_{1-6}$ haloalkoxy, —$OR^{1a}$, —$C(O)R^{1a}$, —$C(O)OR^{1a}$, —$C(O)NR^{1a}R^{1b}$, —$NR^{1a}R^{1b}$, —$SR^{1a}$, —$N(R^{1a})C(O)R^{1b}$, —$N(R^{1a})C(O)OR^{1b}$, —$N(R^{1a})C(O)NR^{1a}R^{1b}$, —$OP(O)(OR^{1a})_2$, —$S(O)_2OR^{1a}$, —$S(O)_2NR^{1a}R^{1b}$, —$S(O)_2$—$C_{1-6}$ haloalkyl, —CN, cycloalkyl, heterocycloalkyl, aryl or heteroaryl. Each of $R^{1a}$ and $R^{1b}$ of Formula I is independently H or $C_{1-6}$ alkyl. Each $R^2$ of Formula I is independently H, halogen, $C_{1-6}$ alkyl, $C_{1-6}$ haloalkyl, $C_{2-6}$ alkenyl, $C_{2-6}$ alkynyl, —$NR^{1a}R^{1b}$, —$NR^{1a}C(O)$—$C_{1-6}$ alkyl, —$NR^{1a}C(O)$—$C_{1-6}$ haloalkyl, —$NR^{1a}$—$(CH_2)$—$NR^{1a}R^{1b}$, —$NR^{1a}$—$C(O)$—$NR^{1a}R^{1b}$, or —$NR^{1a}$—$C(O)OR^{1a}$, alternatively, adjacent $R^1$ groups and adjacent $R^2$ groups can be combined to form a cycloalkyl, heterocycloalkyl, aryl or heteroaryl. $R^3$ of Formula I is —$NR^{3a}R^{3b}$ or —NCO. Each of $R^{3a}$ and $R^{3b}$ of Formula I are independently H, $C_{1-6}$ alkyl, —$C(O)$—$C_{1-6}$ alkyl, —$C(O)$—$C_{1-6}$ haloalkyl, —$(CH_2)$—$NR^{1a}R^{1b}$, —$C(O)$—$NR^{1a}R^{1b}$, —$C(O)OR^{1a}$—$C(S)CN$, an amino acid residue, a peptide or an oligopeptide. Each $R^4$ of Formula I is independently H or $C_{1-6}$ alkyl, or when more than one $R^4$ group is attached to the same atom, the $R^4$ groups are optionally combined to form a $C_{5-8}$ cycloalkyl. The compounds of the present invention also include the salts, hydrates and prodrugs thereof. In this manner, PKCθ is selectively inhibited in the presence of PKCδ.

In a second embodiment, the present invention provides a method of inhibiting cytokine synthesis in a T cell, by administering to a subject in need thereof, a therapeutically effective amount of a compound of Formula I.

In a third embodiment, the present invention provides a method of inhibiting T cell proliferation, by administering to a subject in need thereof, a therapeutically effective amount of a compound of Formula I.

In a fourth embodiment, the present invention provides a method of inhibiting the replication of and cytokine production by T lymphocytes, while not stimulating or inhibiting the replication of B lymphocytes, by administering to a subject in need thereof, a therapeutically effective amount of a compound of Formula I.

DETAILED DESCRIPTION OF THE INVENTION

I. General

Figure 1:
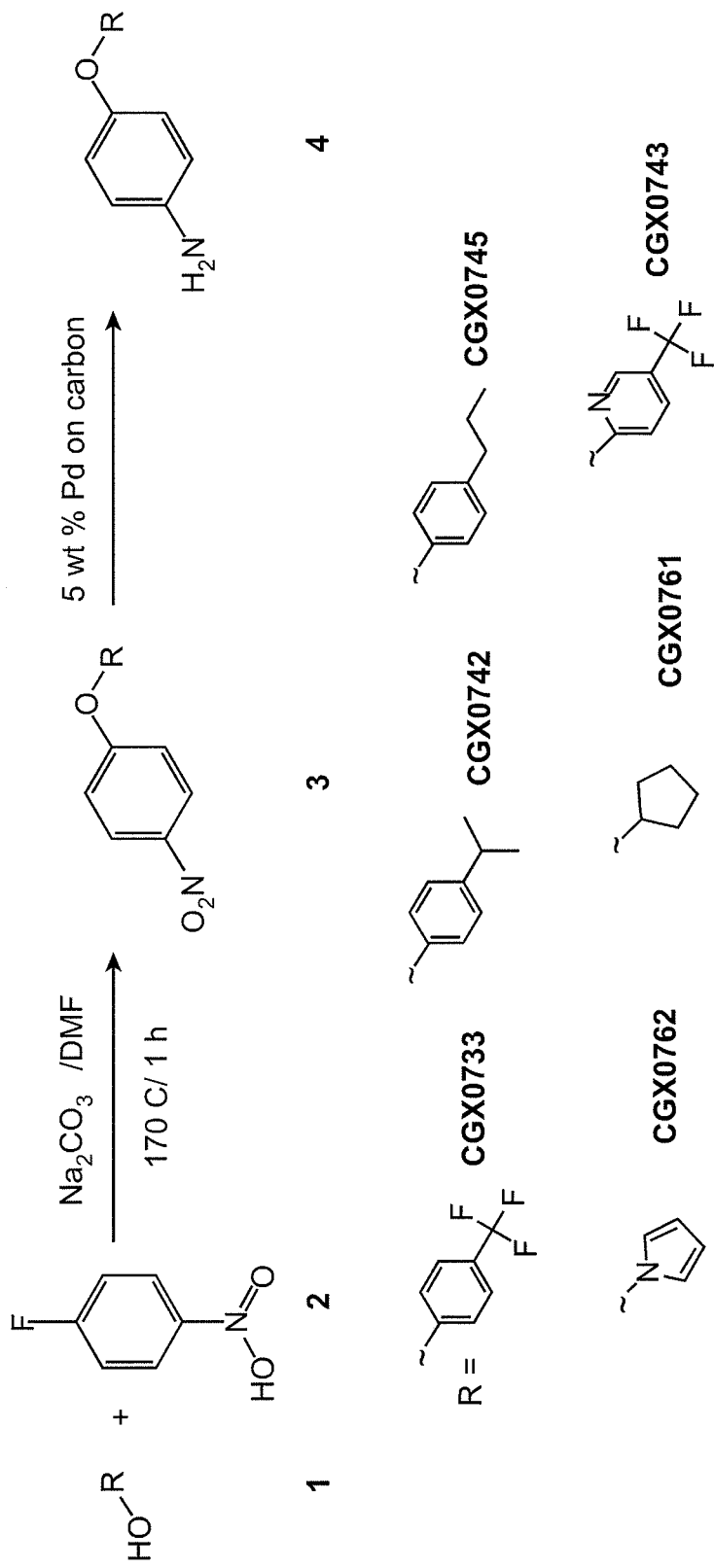
FIG. 1 shows the synthesis of -4-(substituted phenoxy)-anilines (4).

The present invention is drawn to the selective inhibition of protein kinase C-theta (PKCθ) in the presence of other isozymes such as PKCδ. Protein kinase C (PKC) phosphorylates other proteins, thereby altering the function of the protein. Isoforms of PKC include, but are not limited to, α, βI, βII, γ, δ, ε, η, θ, ζ, τ and ξ. PKCθ is involved in T cell activation, which is involved in the proliferation of a variety of diseases. Accordingly, inhibiting T cell activation caused by PKCθ is useful for the treatment of a variety of diseases.

II. Definitions

As used herein, "administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the teems "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As used herein, the term "alkyl" refers to a straight or branched, saturated, aliphatic radical having the number of carbon atoms indicated. For example, $C_1$-$C_8$ alkyl includes, but is not limited to, methyl, ethyl, propyl, iso-propyl, butyl, iso-butyl, sec-butyl, tert-butyl, pentyl, neopentyl, t-pentyl, iso-pentyl, hexyl, heptyl, octyl, etc. In some embodiments, alkyl refers to $C_{1-6}$ alkyl.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —$S(O)_2$—. For example, heteroalkyl includes, but is not limited to, ethers, thioethers and alkyl-amines.

As used herein, the term "haloalkyl" refers to alkyl as defined above where some or all of the hydrogen atoms are substituted with halogen atoms. Halogen (halo) preferably represents chloro or fluoro, but can also be bromo or iodo. For example, haloalkyl includes trifluoromethyl, flouromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl and butynyl.

As used herein, the term "alkoxy" refers to alkyl with the inclusion of an oxygen atom, for example, methoxy, ethoxy, etc. "Haloalkoxy" is as defined for alkoxy where some or all of the hydrogen atoms are substituted with halogen atoms. For example, haloalkoxy includes trifluoromethoxy, etc.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_{3-8}$cycloalkyl includes cyclopropyl, cyclobutyl, cyclopentyl, cyclohexyl, and up to cyclooctyl.

As used herein, the term "heterocycle" refers to a ring system having from 3 ring members to about 20 ring members and from 1 to about 5 heteroatoms such as N, O and S. Preferred heterocycles have 5-10 ring members and 1-4 heteroatoms. More preferred heterocycles have 5-6 ring members and 1-2 heteroatoms. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. Preferred heteroaryls have 5-10 ring members and 1-4 heteroatoms. More preferred heteroaryls have 5-6 ring members and 1-2 heteroatoms. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "halogen" refers to fluorine, chlorine, bromine and iodine.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the term "hydrate" refers to a compound that is complexed to at least one water molecule. The compounds of the present invention can be complexed with from 1 to 10 water molecules.

As used herein, the term "prodrug" refers to covalently bonded carriers which are capable of releasing the active agent of the methods of the present invention, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of the active agents of the present invention include active agents wherein a hydroxy, amidino, guanidino, amino, carboxylic or a similar group is modified.

As used herein, the term "pharmaceutical excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the terms "polypeptide," "peptide," and "protein" are used interchangeably to refer to a polymer of amino acid residues. All three terms apply to amino acid polymers in which one or more amino acid residues is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds. In some instances, amino acid polymers having more than 50 amino acids are referred to as proteins.

As used herein, the term "oligopeptide" refers to a short polymer of amino acid residues, about 2-15. Oligopeptide includes amino acid oligomers in which one or more amino acid residue is an artificial chemical mimetic of a corresponding naturally occurring amino acid, as well as to naturally occurring amino acid oligomers and non-naturally occurring amino acid oligomers.

As used here, the terms "inhibition", "inhibits" and "inhibitor" refer to a compound that prohibits or a method of prohibiting, a specific action or function. "Selectively inhibiting" referes to the inhibition of one species in the presence of another species that is not inhibited. For example, in the present invention, PKCθ is selectively inhibited in the presence of PKCδ, among others.

As used here, the term "amino acid residue" refers to naturally occurring and synthetic amino acids, as well as amino acid analogs and amino acid mimetics that function in a manner similar to the naturally occurring amino acids, that are linked to another moiety, such as via formation of an amide bond. Naturally occurring amino acids are those encoded by the genetic code, as well as those amino acids that are later modified, e.g., hydroxyproline, γ-carboxyglutamate, and O-phosphoserine.

"Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily have the same basic structure as a naturally occurring amino acid. Unnatureal amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

"Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used herein, the term "disease process" refers to a cellular disturbance that gives rise to the symptoms defining a disease.

III. Compounds

The compounds of the present invention include any compound that selectively inhibits PKCθ in the presence of PKCδ. In some embodiments, the compounds of the present invention include those of of Formula I:

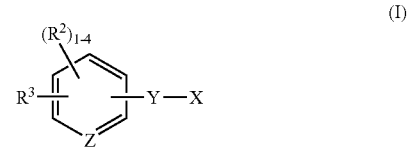

(I)

wherein X of Formula I is aryl or heteroaryl, each substituted with 1-5 $R^1$ groups. Y of Formula I is —O—, —S(O)$_n$—, —N(R$^4$)— and —C(R$^4$)$_2$—, wherein subscript n is 0-2. Z of Formula I is —N= or —CH=. Each $R^1$ of Formula I is independently from the group consisting of H, halogen, $C_{1-8}$ alkyl, $C_{1-6}$ heteroalkyl, $C_{1-6}$ haloalkyl, $C_{2-6}$ alkenyl, $C_{2-6}$ alkynyl, $C_{1-6}$ haloalkoxy, —OR$^{1a}$, —C(O)R$^{1a}$, —C(O)OR$^{1a}$, —C(O)NR$^{1a}$R$^{1b}$, —NR$^{1a}$R$^{1b}$, —SR$^{1a}$, —N(R$^{1a}$)C(O)R$^{1b}$, —N(R$^{1a}$)C(O)OR$^{1b}$, —N(R$^{1a}$)C(O)NR$^{1a}$R$^{1b}$, —OP(O)(OR$^{1a}$)$_2$, —S(O)$_2$OR$^{1a}$, —S(O)$_2$NR$^{1a}$R$^{1b}$, —S(O)$_2$—C$_{1-6}$ haloalkyl, —CN, cycloalkyl, heterocycloalkyl, aryl or heteroaryl. Each of R$^{1a}$ and R$^{1b}$ of Formula I is independently H or $C_{1-6}$ alkyl. Each $R^2$ of Formula I is independently H, halogen, $C_{1-6}$ alkyl, $C_{1-6}$ haloalkyl, $C_{2-6}$ alkenyl, $C_{2-6}$ alkynyl, —NR$^{1a}$R$^{1b}$, —NR$^{1a}$C(O)—C$_{1-6}$ alkyl, —NR$^{1a}$C(O)—C$_{1-6}$ haloalkyl, —NR$^{1a}$—(CH$_2$)—NR$^{1a}$R$^{1b}$, —NR$^{1a}$—C(O)—NR$^{1a}$R$^{1b}$, or —NR$^{1a}$—C(O)OR$^{1a}$, alternatively, adjacent $R^1$ groups and adjacent $R^2$ groups can be combined to form a cycloalkyl, heterocycloalkyl, aryl or heteroaryl. $R^3$ of Formula I is —NR$^{3a}$R$^{3b}$ or —NCO. Each of R$^{3a}$ and R$^{3b}$ of Formula I are independently H, $C_{1-6}$ alkyl, —C(O)—C$_{1-6}$ alkyl, —C(O)—C$_{1-6}$ haloalkyl, —(CH$_2$)—NR$^{1a}$R$^{1b}$, —C(O)—NR$^{1a}$R$^{1b}$, —C(O)OR$^{1a}$, —C(S)CN, an amino acid residue, a peptide or an oligopeptide. Each $R^4$ of Formula I is independently H or $C_{1-6}$ alkyl, or when more than one $R^4$ group is attached to the same atom, the $R^4$ groups are optionally combined to form a $C_{5-8}$ cycloalkyl. The compounds of the present invention also include the salts, hydrates and prodrugs thereof.

In other embodiments, the compounds of the present are those of Formula Ia:

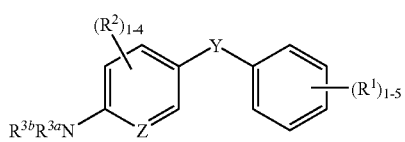

(Ia)

wherein each $R^1$ of Formula Ia is independently H, halogen, $C_{1-8}$ alkyl, $C_{1-6}$ heteroalkyl, $C_{1-6}$ haloalkyl, $C_{2-6}$ alkenyl, $C_{2-6}$ alkynyl, $C_{1-6}$ haloalkoxy, —$OR^{1a}$, —CN, cycloalkyl, heterocycloalkyl, aryl or heteroaryl, and each of $R^{3a}$ and $R^{3b}$ of Formula Ia are independently H, —C(O)—$C_{1-6}$ alkyl, an amino acid residue, a peptide or an oligopeptide. In still other embodiments, each $R^1$ of Formula Ia is independently H, halogen, $C_{1-8}$ alkyl, $C_{1-6}$ haloalkyl, $C_{1-6}$ haloalkoxy, —C(O)$OR^{1a}$, cycloalkyl, or heteroaryl. Furthermore, each $R^2$ of Formula Ia is independently H, halogen, or —$NR^{1a}C(O)$—$C_{1-6}$ alkyl. In yet other embodiments, each $R^1$ of Formula Ia is independently H, methyl, n-propyl, isopropyl, t-butyl, t-pentyl, Cl, Br, $CF_3$, $OCF_3$, cyclopentyl, pyrrolyl, or $CO_2H$, and each $R^2$ is independently H or Cl.

In another embodiment, $R^{3a}$ of Formula I is an amino acid residue, and $R^{3b}$ is H. In other embodiments, the amino acid residue is an arginine residue.

In other embodiments, the compound has Formula Ib:

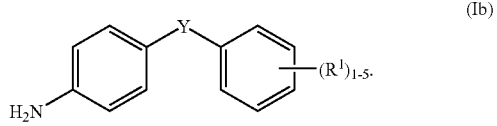

(Ib)

In some other embodiments, Y of Formula Ib is S. In still other embodiments, Y of Formula Ib is O. In some embodiments, each $R^1$ of Formula Ib is independently H, methyl, n-propyl, isopropyl, t-butyl, t-pentyl, Cl, Br, $CF_3$, $OCF_3$, cyclopentyl, pyrrolyl, or $CO_2H$. In yet other embodiments, each $R^1$ of Formula Ib is independently $C_{1-8}$ alkyl or cycloalkyl. In still yet other embodiments, each $R^1$ of Formula Ib is independently 4-t-butyl, 4-cyclopentyl or 4-t-pentyl.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Figure 2:
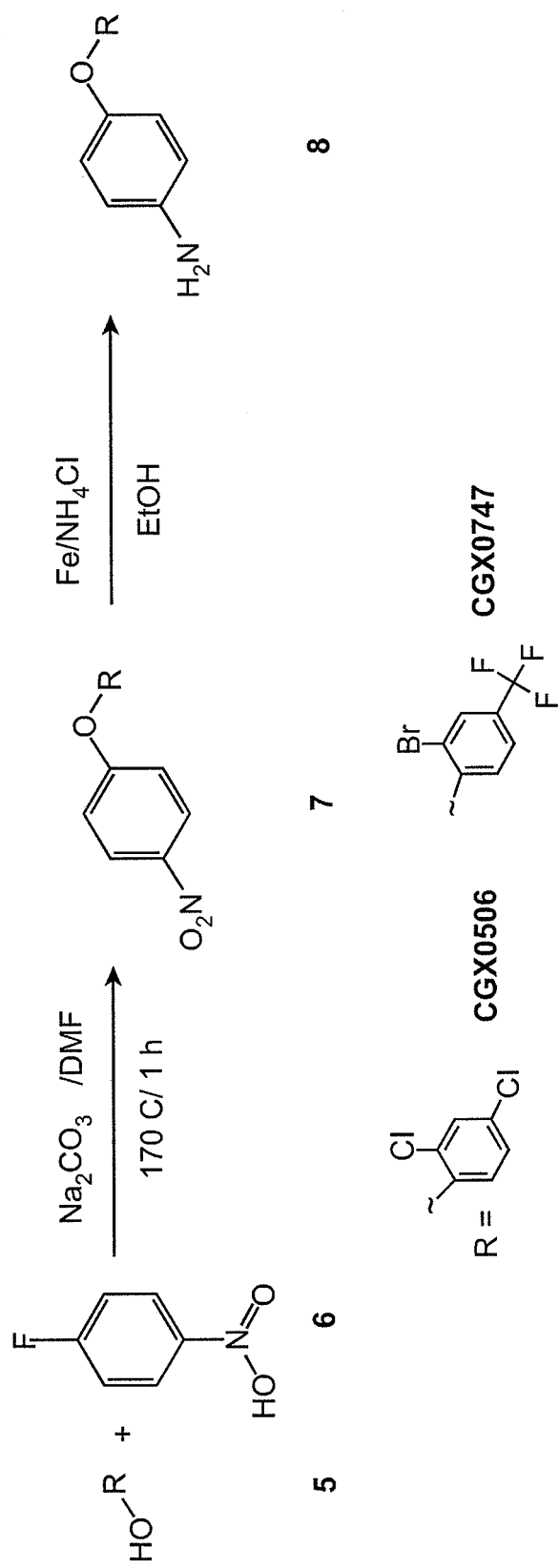
FIG. 2 shows the synthesis of 4-(halogenated phenoxy)-anilines (8).

The compounds of the present invention can be prepared by a variety of methods known to one of skill in the art, such as shown in FIGS. 1-9. One method of preparing the compounds of the present invention involves condensation of a para-fluoro-nitrobenzene with an alcohol, followed by reduction of the nitro group to an amine (FIGS. 1 and 2). A variety of alcohols can be used, such as phenols, heteroaryl alcohols and alkanols, including cycloalkanols. The nitro group can be reduced by a variety of reagents known to one of skill in the art, including, but not limited to, Pd/C and Fe/$NH_4Cl$. In addition to the aryl-nitro starting material shown in FIG. 1, heteroaryl-nitro compounds can also be used in the condensation method to prepare compounds of the present invention. One of skill in the art will appreciate that other alcohols and reduction steps are useful in preparing the compounds of the present invention.

Figure 3:
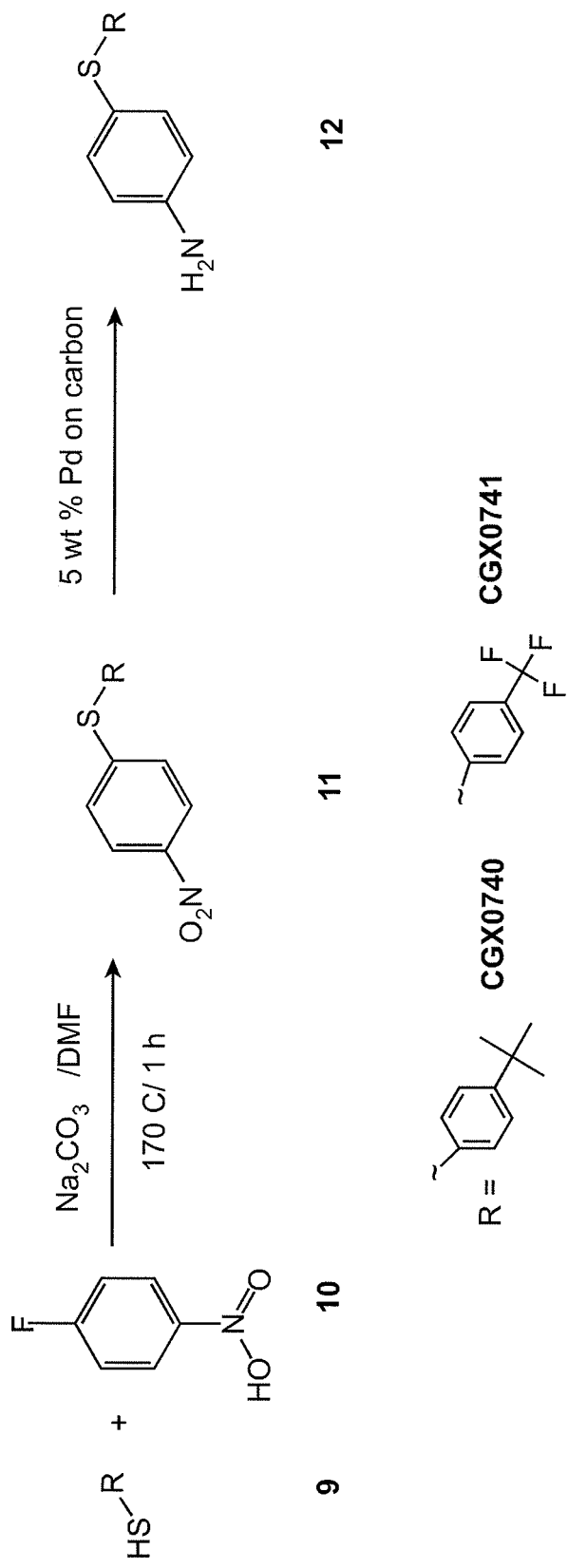
FIG. 3 shows the synthesis of 4-(substituted phenylthio)-anilines (12).
Figure 4:
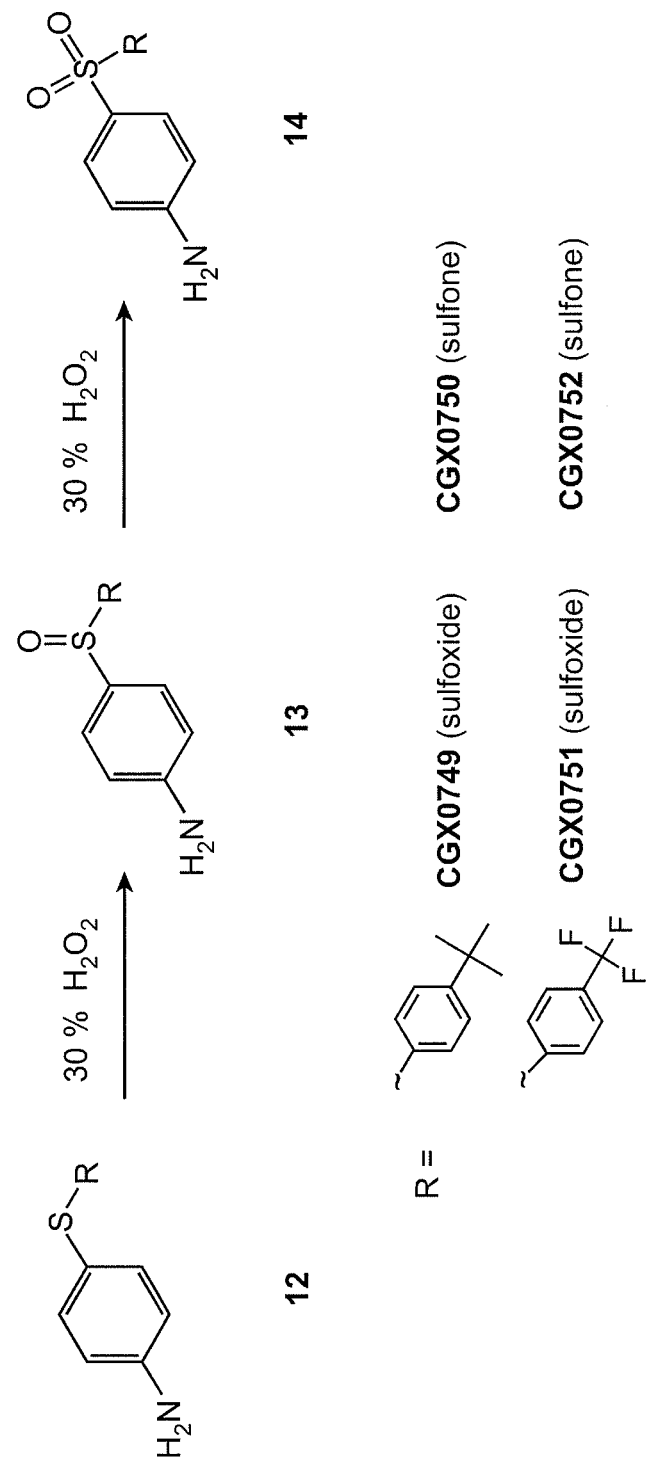
FIG. 4 shows the synthesis of 4-[substituted (phenylsulfinyl and phenylsulfonyl)]-anilines (13 and 14, respectively).
Figure 5:
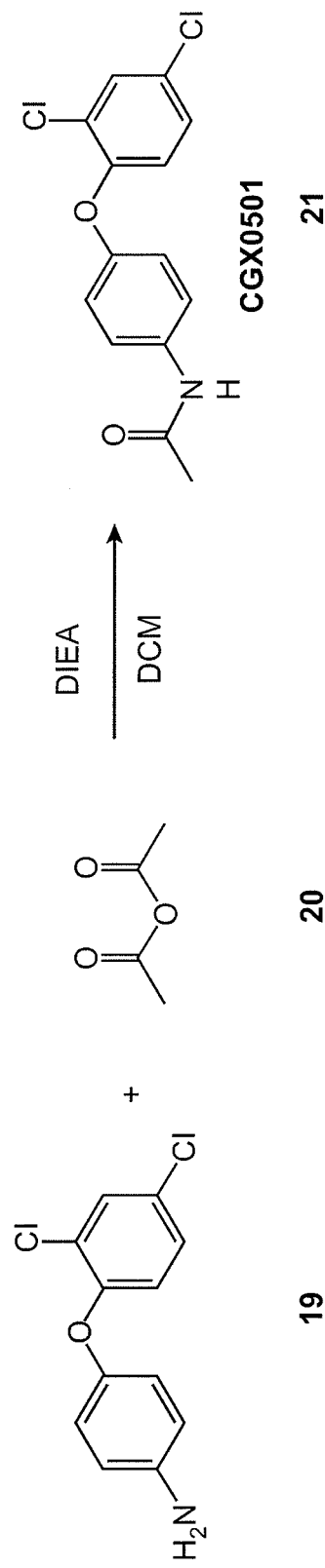
FIG. 5 shows the synthesis of N-acylated aniline-2,4-dichlorophenyl ether.
Figure 8:
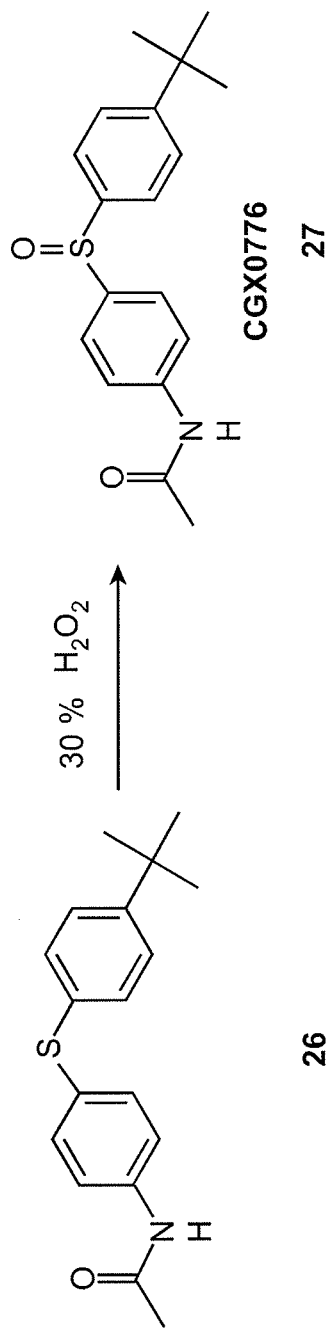
FIG. 8 shows the synthesis of N-acylated 4-[substituted (phenylsulfinyl and phenylsulfonyl)]-anilines.

The condensation method can also be used with thiols to prepare a disulfide (FIG. 3). The nitro group can be reduced as previously described. Thiols useful in the condensation method for making compounds of the present invention include, but are not limited to, thiophenols. The disulfide can also be oxidized to the sulfoxide and the sulfone using any oxidizing agent known to one of skill in the art, including, but not limited to, hydrogen peroxide (FIGS. 4 and 8). One of skill in the art will appreciate that other oxidizing agents are useful in the present invention.

Figure 6:
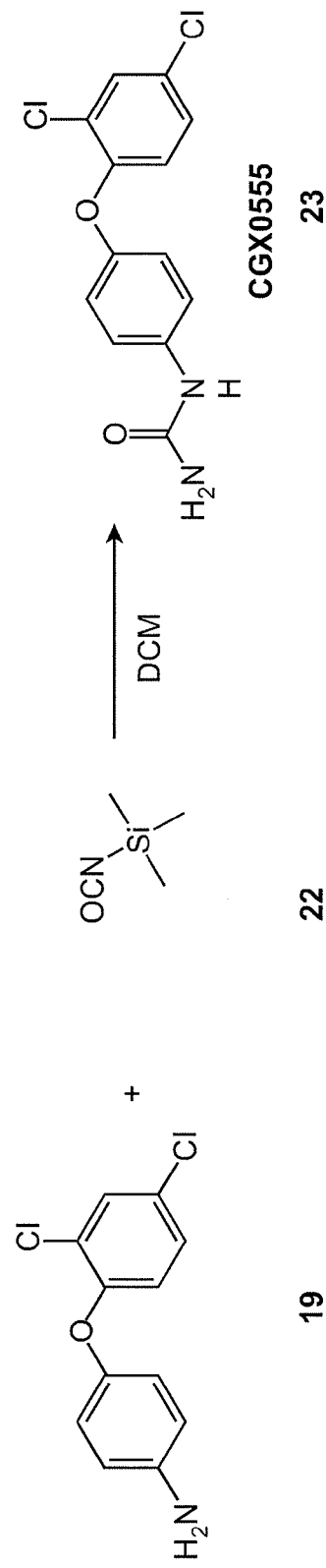
FIG. 6 shows the synthesis of N-(2,4-dichlorophenoxyphenyl)urea.
Figure 7:
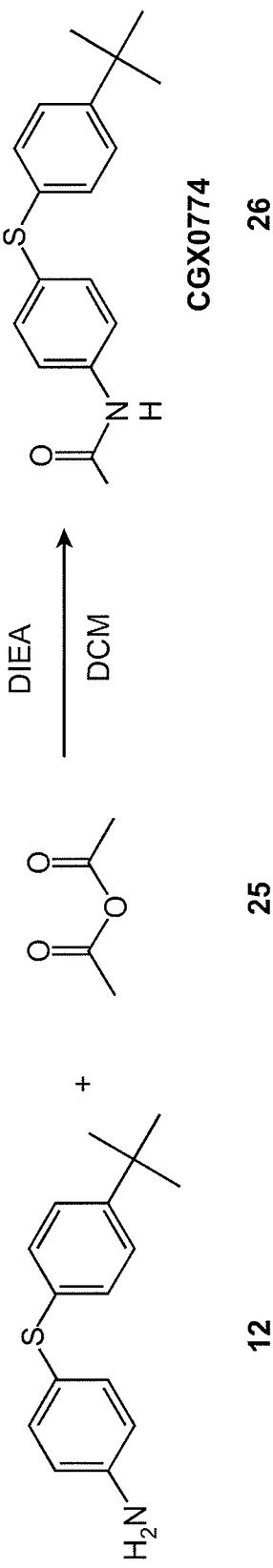
FIG. 7 shows the synthesis of N-acylated 4-(substituted phenylthio)anilines ether and 4-(tert-butylphenylthio)acetanilide (26).
Figure 9:
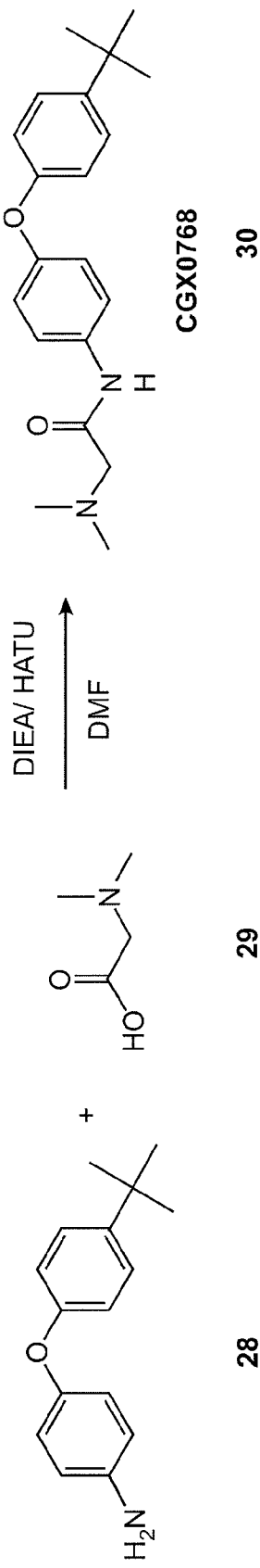
FIG. 9 shows the synthesis of 4'-(tert-butylphenoxy)-2-dimethylaminoacetanilide.

The amine group of the compounds of the present invention can be derivatized by a variety of methods known to one of skill in the art. In some embodiments, the amine can be acylated such as with an anhydride (FIGS. 5 and 7) or by condensation with a carboxylic acid (FIG. 9). In other embodiments, the amine can be reacted with an isocyanate to afford the urea (FIG. 6). Additional methods of making the compounds of the present invention are known to one of skill in the art, for example, those described in *Comprehensive Organic Transformations*, 2d ed., Richard C. Larock, 1999, and methods described in U.S. Pat. No. 4,130,433, incorporated in its entirety herein. The starting materials for the methods described above are commercially available (Sigma-Aldrich) or can be prepared by methods known to one of skill in the art.

The starting materials used in the synthetic methods described above can be substituted or unsubstituted. Substituents for starting materials include, but are not limited to, -halogen, —OR', —OC(O)R', —NR'R", —SR', —R', —CN, —$NO_2$, —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, perfluoro($C_1$-$C_4$)alkoxy, and perfluoro($C_1$-$C_4$)alkyl, cycloalkyl, heterocycloalkyl, aryl and heteroaryl, where R', R" and R'" are independently selected from hydrogen and ($C_1$-$C_8$)alkyl.

One of skill in the art will appreciate that certain compounds of the present invention possess asymmetric carbon atoms (optical centers) or double bonds; the racemates, diastereomers, geometric isomers and individual isomers are all intended to be encompassed within the scope of the present invention.

IV. Methods of Identifying Compounds as Selectively Inhibiting PKCθ in the presence of PKCδ

Using the XenoGene™ system described within, compounds inhibiting PKCθ are identified. The XenoGene™ system is a technology developed and patented by CompleGen wherein genes ("XenoGenes"™) from a target organism (e.g. humans) are used to functionally replace essential genes of a simple organism (yeast). These modified yeast are used to select compounds that act specifically on the protein encoded by the target gene and eliminate compounds that are not specific. XenoGene™ constructs provide a very high throughput screening system that allows identification of compounds active on the function of the target protein in a cell under physiological conditions on "first-pass" screening and further, to selectively counter-screen against 200 human targets or more if necessary. The "read out" of the XenoGene™ assay is simply growth (inactive compound) or no growth (active compound) of the yeast containing the target gene, and growth of control strains that do not contain the target gene. The relative potencies of the active compounds is determined by titration to find the concentration of compound providing 50% inhibition of growth ($IC_{50}$) against the yeast containing the target gene (Table 1).

TABLE I $IC_{50}$ Values for Compounds of Formula Ia

| Compound | $R^1$ | $R^2$ | $R^{3a}$ | $R^{3b}$ | Y | Z | $IC_{50}$[1] |
|---|---|---|---|---|---|---|---|
| 471 | 4-t-butyl | H | H | H | O | —CH= | +++ |
| 486 | 4-t-butyl | H | H | H | O | —N= | + |
| 498 | 2-Cl, 4-OCF$_3$ | H | H | H | O | —CH= | +++ |
| 499 | 2-Cl, 4-CF$_3$ | H | H | H | O | —CH= | +++ |
| 500 | H | H | H | H | O | —CH= | + |
| 501 | 2,4-Cl$_2$ | H | C(O)Me | H | O | —CH= | + |
| 503 | 2-Cl, 4-OCF$_3$ | 3-Cl | H | H | O | —CH= | ++ |
| 504 | 3,5-Cl$_2$ | H | H | H | O | —CH= | ++ |
| 505 | 4-Cl, 3-CH$_3$ | H | H | H | O | —CH= | +++ |
| 506 | 2,4-Cl$_2$ | H | H | H | O | —CH= | ++ |
| 507 | 4-Cl, 3-CH$_3$ | H | H | H | O | —CH= | ++ |
| 508 | 4-CH$_3$ | H | H | H | O | —CH= | ++ |
| 509 | 3,5-Cl$_2$ | H | H | H | O | —CH= | ++ |
| 510 | 4-OCF$_3$ | H | H | H | O | —CH= | +++ |
| 553 | 2-COOH | H | H | H | O | —CH= | + |
| 730 | 4-t-pentyl | H | H | H | O | —CH= | +++ |
| 733 | 4-CF$_3$ | H | H | H | O | —CH= | ++ |
| 740 | 4-t-butyl | H | H | H | S | —CH= | +++ |
| 741 | 4-CF$_3$ | H | H | H | S | —CH= | +++ |
| 742 | 4-isopropyl | H | H | H | O | —CH= | +++ |
| 745 | 4-n-propyl | H | H | H | O | —CH= | +++ |
| 747 | 2-Br, 4-CF$_3$ | H | H | H | O | —CH= | +++ |
| 749 | 4-t-butyl | H | H | H | SO$_2$ | —CH= | ++ |
| 750 | 4-t-butyl | H | H | H | SO$_2$ | —CH= | + |
| 751 | 4-CF$_3$ | H | H | H | SO | —CH= | + |
| 753 | 4-CF$_3$ | H | H | H | SO$_2$ | —CH= | ++ |
| 761 | 4-cyclopentyl | H | H | H | O | —CH= | +++ |
| 762 | 1-pyrrolyl | H | H | H | O | —CH= | ++ |

[1]+++, <1 µM; ++, 1-10 µM; +, >10 µM.

To identify compounds as being selective PKC theta inhibitors the $IC_{50}$ values are determined against XenoGene™ strains containing other XenoGenes™, especially certain other PKC genes (see Example 10). One of skill in the will appreciate that other compounds of the present invention selectively inhibit PKCθ in the presence of PKCδ.

V. Method of Selectively Inhibiting PKCθ in the presence of PKCδ

In some embodiments, the present invention provides a method of selectively inhibiting PKCθ in the presence of PKCδ, by administering to a subject in need thereof, a therapeutically effective amount of a compound of Formula I:

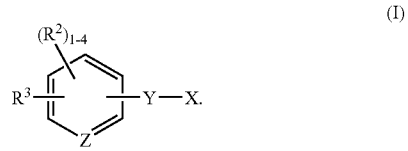

A. Formulations

The compounds of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003). Effective formulations include oral and nasal formulations, formulations for parenteral administration, and compositions formulated for with extended release.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Pharmaceutical preparations useful in the present invention also include extended-release formulations. In some embodiments, extended-release formulations useful in the present invention are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present invention, the pharmaceutical compositions can be used alone, or in combination with other therapeutic or diagnostic agents.

B. Administration

The compounds of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

C. Treatment of Diseases

The method of the present invention can be used to treat a variety of diseases and conditions involving PKCθ, including, but not limited to, inflammatory diseases (uveitis, psoriasis, rheumatoid arthritis, multiple sclerosis, inflammatory bowel syndrome, Crohn's disease), atopic dermatitis, prevention of organ transplant rejection, T cell lymphomas and leukemia, diseases involving degranulation of basophilic granulocytes and reversal of insulin resistant type II diabetes.

VI. Inhibition of the Activation of Effector T cells

In some embodiments, the present invention provides a method of inhibiting cytokine synthesis in a T cell, by administering to a subject in need thereof, a therapeutically effective amount of a compound of Formula I. In other embodiments, the compound is of Formula Ib. In some other embodiments, X of Formula Ib is S. In still other embodiments, X of Formula Ib is O.

In other embodiments, the present invention provides a method of inhibiting T cell proliferation, by administering to a subject in need thereof, a therapeutically effective amount of a compound of Formula I. In some embodiments, the compound is of Formula Ib. In some other embodiments, X of Formula Ib is S. In still other embodiments, X of Formula Ib is O.

In some other embodiments, the present invention provides a method of inhibiting the replication of and cytokine production by T lymphocytes, while not stimulating or inhibiting the replication of B lymphocytes, by administering to a subject in need thereof, a therapeutically effective amount of a compound of Formula I. In other embodiments, the compound is of Formula Ib. In some other embodiments, X of Formula Ib is S. In still other embodiments, X of Formula Ib is O.

Compounds useful in the method of inhibiting cytokine synthesis in a T cell or inhibiting T cell proliferation are identified by their ability to inhibit antigen-specific T cell activation. Assays for inhibiting antigen-specific T cell activation are known to one of skill in the art. In some embodiments, the assay involves immunizing mice with ovalbumin, isolating mouse splenic T cells and incubating the isolated cells with mitomycin C treated, unimmunized mouse spleen cells or T cell depleted spleen cells. Proliferation was measured by incorporation of $^3$H-TdR (see Example 11). One of skill in the art will appreciate that other assays are useful in the present invention.

The compounds of the present invention can also be screened for the ability to inhibit T cell lymphomas. Assays for inhibiting T cell lymphomas are known to one of skill in the art. In some embodiments, the assay involves mice generated from the nucleus of a mature T cell with a "fixed" rearranged T cell receptor. These T cells spontaneously generate T cell lymphomas which resemble human T cell lymphomas. T cell lymphomas isolated from the mice can then be treated with compounds of the present invention. After sufficient time to allow for cell growth, live cells are counted by flow cytometry (Serwold et al. (2007) J. Immunol. 179;928). One of skill in the art will appreciate that other assays are useful in the present invention.

VII. EXAMPLES

Example 1

Synthesis of 4-(substituted phenoxy)-anilines (4)

In a 5 mL microwave tube, 200 mg of the substituted phenol (1) and 1 equiv. of 1-fluoro-4-nitrobenzene (2) were dissolved in 4 mL of DMF and 2.9 equiv. of Na$_2$CO$_3$ was added. The reaction mixture was heated in the microwave at 170° C. for 1 h. The mixture was extracted with EtOAc and water; the organic phase was washed with brine and dried over MgSO$_4$. The EtOAc was evaporated on the rotary evaporator to give the crude product (3). (60-70% yield).

In a hydrogenation bottle, crude (3) was dissolved in MeOH; solution was purged with N$_2$ prior to the addition of 50-100 mg of 5 wt % Pd on activated carbon. The reaction mixture was placed in a hydrogenator and shaken with 1-2 atm H$_2$ for 1-2 hr. Upon completion of the reaction, the catalyst was filtered through the fritted funnel and was rinsed with MeOH. MeOH was evaporated using the rotary evaporator to give the final crude product (4). (Approx. 80% yield).

Example 2

Synthesis of 4-(halogenated phenoxy)-anilines (8)

In a 5 mL microwave tube, 200 mg of the substituted phenol (5) and 1 equiv. of 1-fluoro-4-nitrobenzene (6) were dissolved in 4 mL of DMF, then 2.9 equiv. of $Na_2CO_3$ was added. The reaction mixture was allowed to heat in the microwave at 170° C. for 1 h. The mixture was partitioned between EtOAc and water; the organic phase was washed with brine and then dried over $MgSO_4$. The EtOAc was evaporated by the rotary evaporator to give the crude product (7). (Approx. 70-90% yield).

In a round bottom flask, crude (7) was dissolved in 50 L of EtOH; 15 equiv. of Fe powder and 25 mL of saturated aqueous $NH_4Cl$ were added to the solution mixture. The reaction mixture was allowed to reflux at 90° C. for 2 h. Fe powder was filtered from the reaction mixture with a fritted funnel. The filtrate was concentrated using the rotary evaporator. Crude product was extracted with EtOAc and water; the organic phase was washed with brine and then dried over $MgSO_4$. The solvent was removed on the rotary evaporator, giving approximately 65-85% yield of crude product (8).

Example 3

Synthesis of 4-(substituted phenylthio)-anilines (12)

In a 5 mL microwave tube, 200 mg of the substituted thiol (9) and 1 equiv. of 1-fluoro-4-nitrobenzene (10) were dissolved in 4 mL of DMF, then 2.9 equiv. of $Na_2CO_3$ was added. The reaction mixture was heated in the microwave at 170° C. for 1 h. The mixture was partitioned between EtOAc and water; the organic phase was washed with brine and then dried over $MgSO_4$. EtOAc was evaporated on the rotary evaporator to give the crude product (11). (60-70% yield).

In a hydrogenation bottle, crude (11) was dissolved in MeOH; solution was purged with $N_2$ prior to the addition of 50-100 mg of 5 wt % Pd on activated carbon. The reaction mixture was hydrogenated for 1 hr; reaction course monitored by LC/MS. Upon completion of the reaction, Pd was filtered through a fitted funnel and was rinsed with MeOH. MeOH was evaporated on the rotary evaporator to give the final crude product (12). (40-50% yield).

Example 4

Synthesis of 4-[substituted (phenylsulfinyl and phenylsulfonyl)]-anilines (13 and 14, Respectively)

In a round bottom flask, crude (12) was dissolved in 1 mL of DMF. Excess of 30% $H_2O_2$ solution (approx. 3-5 mL) was subsequently added to the solution. The reaction mixture was allowed to sit at room temperature for 24 h; reaction course was monitored by LC/MS. Reaction mixture was concentrated by the rotary evaporator to give the final crude sulfoxide (13).

Sulfone was obtained by the addition of excess of 30% $H_2O_2$ solution (another 3-5 mL). The reaction mixture was allowed to sit at R.T. for 72 h to afford the final product (14). Reaction course was monitored by LC/MS.

Example 5

Synthesis of N-acylated aniline-2,4-dichlorophenyl ether

In a 20 mL vial, 4-(2,4-dichlorophenoxy)aniline (19) and 1 equiv. of acetic anhydride (20) were dissolved in 3 mL of dichloromethane, followed by the addition of 1 equiv. of diisopropylethylamine. The reaction mixture was allowed to stir at R.T. for 2 h. dichloro methane (DCM) was then evaporated by the rotary evaporator to give the desired product (21).

Example 6

Synthesis of N-(2,4-dichlorophenoxyphenyl)urea

In a 20 mL vial, aniline-2,4-dichlorophenyl ether (19, 506) was dissolved in 3 mL of dichloromethane and 2 equiv. of trimethylsilyl isocyanate (22) was added. The reaction mixture was allowed to stir at 40° C. for 48 h; reaction course was monitored by LC/MS. Precipitates were filtered through the fritted funnel, washed with DCM several times, and then air-dried to afford the desired pure product (23). Exact Mass=296; observed mass=296.7 (28% yield).

Example 7

Synthesis of N-acylated 4-(substituted phenylthio)anilines ether, 4-(tert-butylphenylthio)acetanilide (26)

In a 20 mL vial, 12 was dissolved in 5 mL of DCM. 1 equiv. of acetic anhydride (25) and 1 equiv. of DIEA were added. The reaction mixture was allowed to stir at 40° C. for 24 h. Solvent was removed by the rotary evaporator to afford (26).

Example 8

Synthesis of N-acylated 4-[substituted (phenylsulfinyl and phenylsulfonyl)]-anilines In a 50 mL round bottom flask, 26 was dissolved in 1 mL of DMF prior to subsequent addition of 3-5 mL of 30% $H_2O_2$ solution. The reaction was allowed to stir at R.T. for 48 h, then at 35° C. for 4 h. Crude product was extracted with EtOAc and water; organic phase was washed with brine and dried over $MgSO_4$. EtOAc was evaporated using the rotary evaporator to give 27.

Example 9

Synthesis of 4'-(tert-butylphenoxy)-2-dimethylaminoacetanilide

In a 50 mL round bottom flask, (28) and 1 equiv. of N,N-dimethylglycine (29) were dissolved in 5 mL of DMF, followed by the addition of 3 equiv. of diisopropylethylamine and 1.3 equiv. of HATU (O-(7-Azabenzotriazole-1-yl)-N,N,N'N'-tetramethyluronium hexafluorophosphate). The reaction mixture was stirred at R.T. for 48 h. The mixture was diluted with EtOAc and crude product was extracted with 5% $NaHCO_3$ solution twice. Organic phase was washed with brine and then dried over $MgSO_4$. EtOAc was evaporated using the rotary evaporator to afford (30). (30% yield).

Example 10

Identification of Compounds with Selective PKCθ Inhibition Activity

Human PKC theta gene (cDNA) was used to generate a XenoGene™ system as previously described (U.S. Pat. Nos. 6,998,261, 6,232,074), which was used to screen compounds in a chemical compound library. XenoGene™ systems used as counter-screens were constructed similarly using the gene for the appropriate counter-screen target. In particular, human genes (cDNA) encoding PKC delta, PKC eta and PKC episilon were used to generate XenoGene™ systems.

Using the XenoGene™ system, the following compounds were identified as being selective PKC theta inhibitors.

| Target/ Compound | PKC-theta $IC_{50}$ (µM) | Selectivity for PKC-theta v.[1] | | | |
|---|---|---|---|---|---|
| | | PKC- delta | PKC- epsilon | PKC- eta | yeast PKC1 |
| 471 | 0.14 | 2.5 | 1.1 | 0.36 | 28 |
| 504 | 1.6 | 8.1 | 8.8 | 1.8 | |
| 505 | 0.40 | 13 | 11 | 3.0 | |
| 506 | 1.6 | 1.9 | 2.5 | 0.63 | 9.4 |
| 740 | 0.05 | 26 | 12 | 3.0 | 80 |
| 741 | 0.25 | 8.0 | 16 | 4.0 | 32 |

[1]These values are calculated by taking the inverse of the ratio of (PKC-theta $IC_{50}$)/(PKC-X $IC_{50}$).

Example 11

Inhibition of Effector T cells

The compounds of the present invention were tested for their ability to inhibit the activation of effector T cells. The procedures described are familiar to scientists skilled in immunological research and references are given as examples, but, are not meant to be limiting.

Inhibition of antigen-specific (effector) T cell activation (cellular proliferation and cytokine production). Mice were immunized i.p at least 2 weeks in advance with 100 mg soluble OVA (ovalbumin, Sigma) emulsified 1:1 in CFA (complete Freund's adjuvant, Sigma). Mouse splenic T cells were isolated by magnetic negative selection (Miltenyi®, Untouched T Cell Isolation Kit) or FACS using anti-CD3-PE-Cy7. 105 isolated T cells were incubated in microtiter wells with 105 mitomycin C treated, unimmunized mouse spleen cells or T cell depleted spleen cells as Antigen Presenting Cells (APC) and 1 mg soluble OVA in 100 microliters 10% FBS-RPMI for five days. Results were similar with mitomycin C-treated total spleen cells and mitomycin C-treated, T depleted spleen cells. Proliferation was measured by incorporation of $^3$H-TdR, added for the final 18 hrs of culture. The mitomycin C treated spleen cells or T-depleted spleen cells consistently yielded only background levels of $^3$H-TdR. Mononuclear spleen cells were isolated from Mice (See Dubey, C. et al. (1995) J. Immunol. 155;45). T cell proliferation was measured by $^3$H-TdR incorporation. Cytokine production was measured by the CBA® multiplexed assay system (BD Biosciences) according to manufacturer's directions.

Inhibition of naïve T cell activation by compound 471. Mouse splenic T cells were isolated from unimmunized mice by magnetic negative selection (Miltenyi®, Untouched T Cell Isolation Kit) or FACS using anti-CD3-PE-Cy7. Isolated T cells were incubated in microtiter wells coated with anti-CD3 monoclonal antibody and soluble anti-CD28 monoclonal antibody, $10^5$ cells/1000 µl in 10% FBS-RPMI as above, for three days. Proliferation was measured by $^3$H-TdR incorporation.

| Compound | $^3$H-TdR cpm |
|---|---|
| 0 | 31571 |
| 0.5 uM | 21928 |
| 1.0 uM | 880 |

Inhibition of T cell lymphomas. Mice generated from the nucleus of a mature T cell (see Hochedlinger K, Jaenisch R. (2002) Nature 415;1035) with a "fixed" rearranged T cell receptor spontaneously generate T cell lymphomas which resemble human T cell lymphomas. Several T cell lymphomas (1-4) isolated from these mice were treated with compound 471. All T cell lymphomas were inhibited by compound 471. A B-cell hybridoma served as a non-T cell control and was not affected by the compound. Cells were seeded into 96-well plates (5,000 cells/well) in the presence of compound 471 at concentrations ranging from 0.1 to 5 uM. After 4 days growth (37° C., 5% $CO_2$), live cells were counted by flow cytometry (Serwold et al. (2007) J. Immunol. 179;928)

| | Cell Type | | | | |
|---|---|---|---|---|---|
| | Lym- phoma 1 | Lym- phoma 2 | Lymphoma 4 | Lymphoma 5 | B-cell Hybridoma |
| $EC_{50}$ | 0.7 uM | 0.2 uM | <0.1 uM | 0.7 uM | >5 uM |

Lack of activity on B-lymphocytes. Mouse splenic B cells were isolated by negative magnetic selection (Miltenyi®, Untouched T Cell Isolation Kit) or FACS using anti-CD 19-PE. Isolated B cells were incubated in microtiter wells with soluble anti-IgM and anti-CD40 monoclonal antibodies, $10^5$ cells/100 µl in 10% FBS-RPMI as above, for three days. Proliferation was measured by $^3$H-TdR incorporation.

Figure 10:
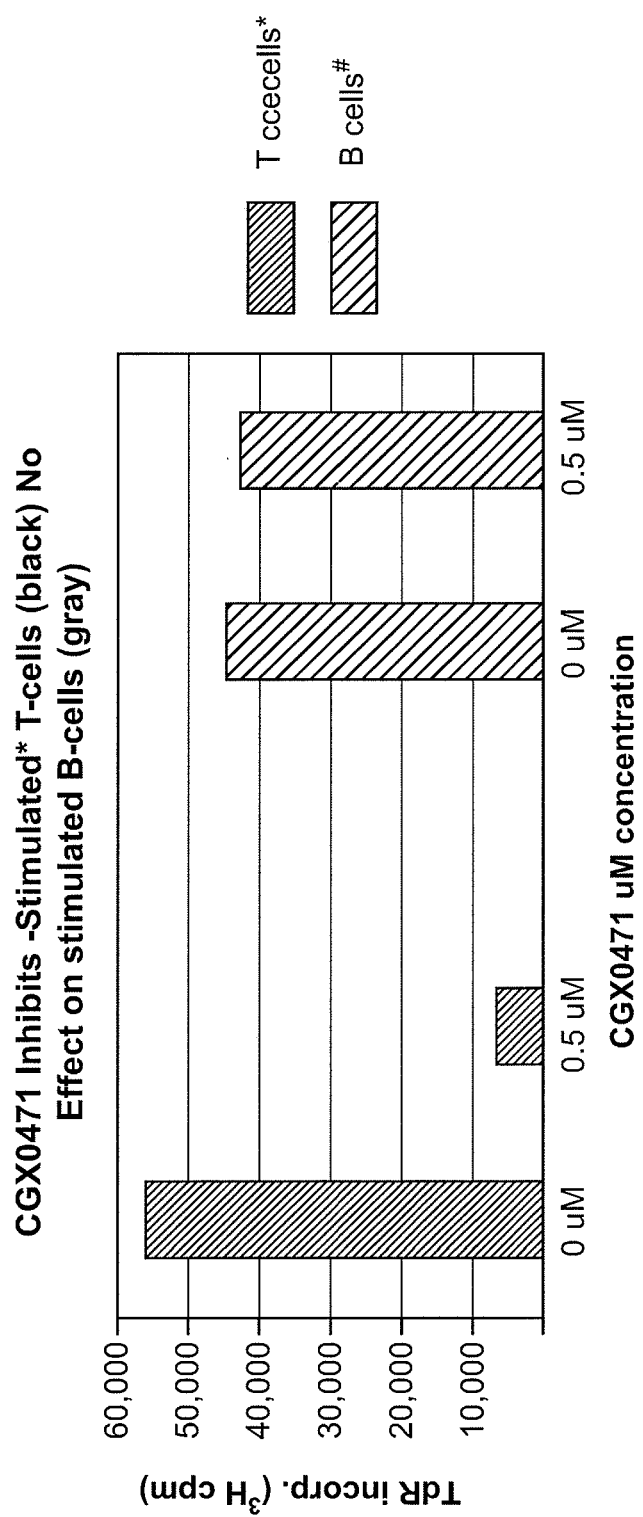
FIG. 10 shows B-cells DNA synthesis was normal in the presence of PKC theta inhibitor compounds.
Figure 11:
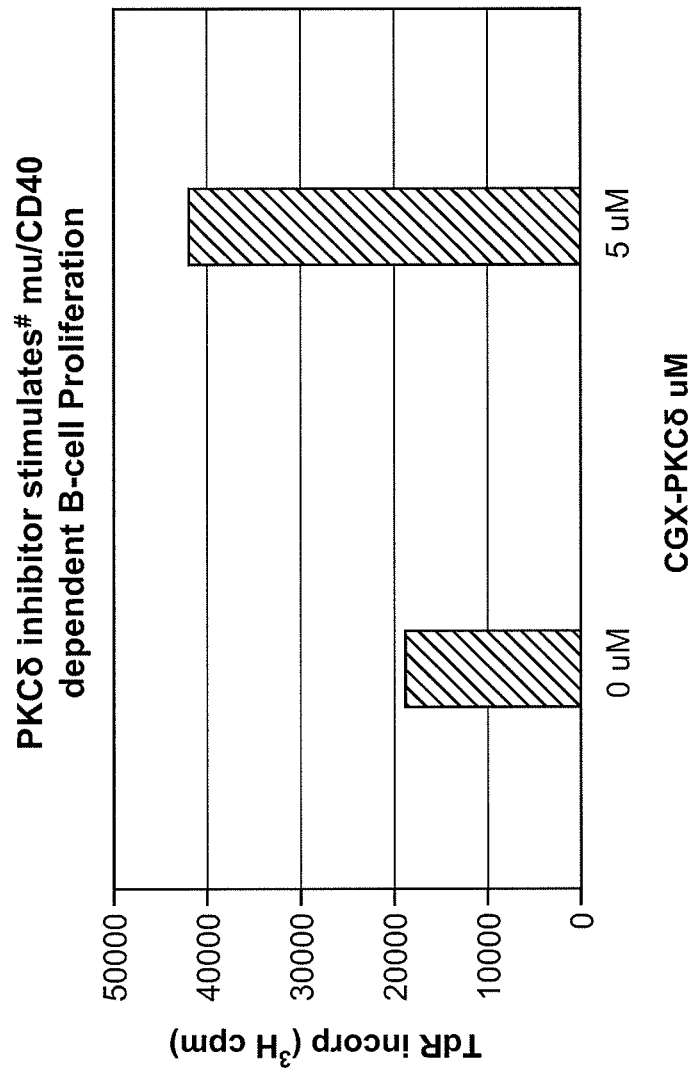
FIG. 11 shows B-cell proliferation was "hyperstimulated" by a PKC delta inhibitor.

As shown in FIG. 10, B-cells DNA synthesis was normal in the presence of PKC theta inhibitor compounds. As shown in FIG. 11, B-cell proliferation was "hyperstimulated" by a PKC delta inhibitor.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of inhibiting T cell proliferation, comprising the step of administering to a subject in need thereof, a therapeutically effective amount of a compound of Formula Ib:

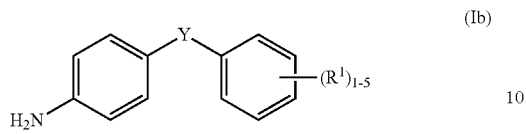

(Ib)

wherein
Y is selected from the group consisting of —O— and —S—;
each $R^1$ is independently selected from the group consisting of n-propyl, isopropyl, t-butyl, t-pentyl, $CF_3$, $OCF_3$, cyclopentyl, pyrrolyl, and $CO_2H$;
and salts, hydrates and prodrugs thereof, thereby inhibiting T cell proliferation.

2. The method of claim 1, wherein Y is O.

3. The method of claim 1, wherein the T cell proliferation is part of a disease process selected from the group consisting of inflammatory diseases, organ transplant rejection, and insulin resistant type II diabetes.

4. The method of claim 1, wherein each $R^1$ is independently selected from the group consisting of 4-t-butyl, 4-cyclopentyl and 4-t-pentyl.

* * * * *